United States Patent [19]

Bornn et al.

[11] Patent Number: 4,827,943

[45] Date of Patent: May 9, 1989

[54] PORTABLE, MULTI-CHANNEL, PHYSIOLOGICAL DATA MONITORING SYSTEM

[75] Inventors: Robert Bornn, Los Altos Hills; Robert D. Ricks, Newark, both of Calif.

[73] Assignee: Advanced Medical Technologies, Inc., Los Altos, Calif.

[21] Appl. No.: 109,261

[22] Filed: Oct. 15, 1987

Related U.S. Application Data

[63] Continuation-in-part of Ser. No. 910,457, Sep. 23, 1986, abandoned.

[51] Int. Cl.$^4$ ............................................... A61B 5/02
[52] U.S. Cl. .................................... 128/668; 128/903
[58] Field of Search ............... 128/903, 668, 671, 782, 128/774

[56] References Cited

U.S. PATENT DOCUMENTS 3,478,344 11/1969 Schwitzgebe et al. ............ 128/903
3,572,316 3/1971 Vogelman et al. ................ 128/671
4,503,862 3/1985 Baessler ............................ 128/903

Primary Examiner—Francis Jaworski
Assistant Examiner—George Manuel
Attorney, Agent, or Firm—Limbach, Limbach & Sutton

[57] ABSTRACT

The system of the present invention provides a link between the caregiver and the subject being monitored which utilizes an intermediate base station and redundant signal paths between the base station and the caregiver. The caregiver wears a unit which receives signals from the base station. Signals from the base station provide information about the subject being monitored and provide signals for use in determining whether the caregiver remains within the range of the base station. The unit worn by the subject being monitored can include diagnostic circuitry for evaluating signals received from sensors to transmit an alarm signal to the base station when the subject being monitored is in need of assistance. A range monitoring system is provided which will alert the subject being monitored as well as the caregiver whenever the subject being monitored moves outside the range of the base station.

7 Claims, 15 Drawing Sheets

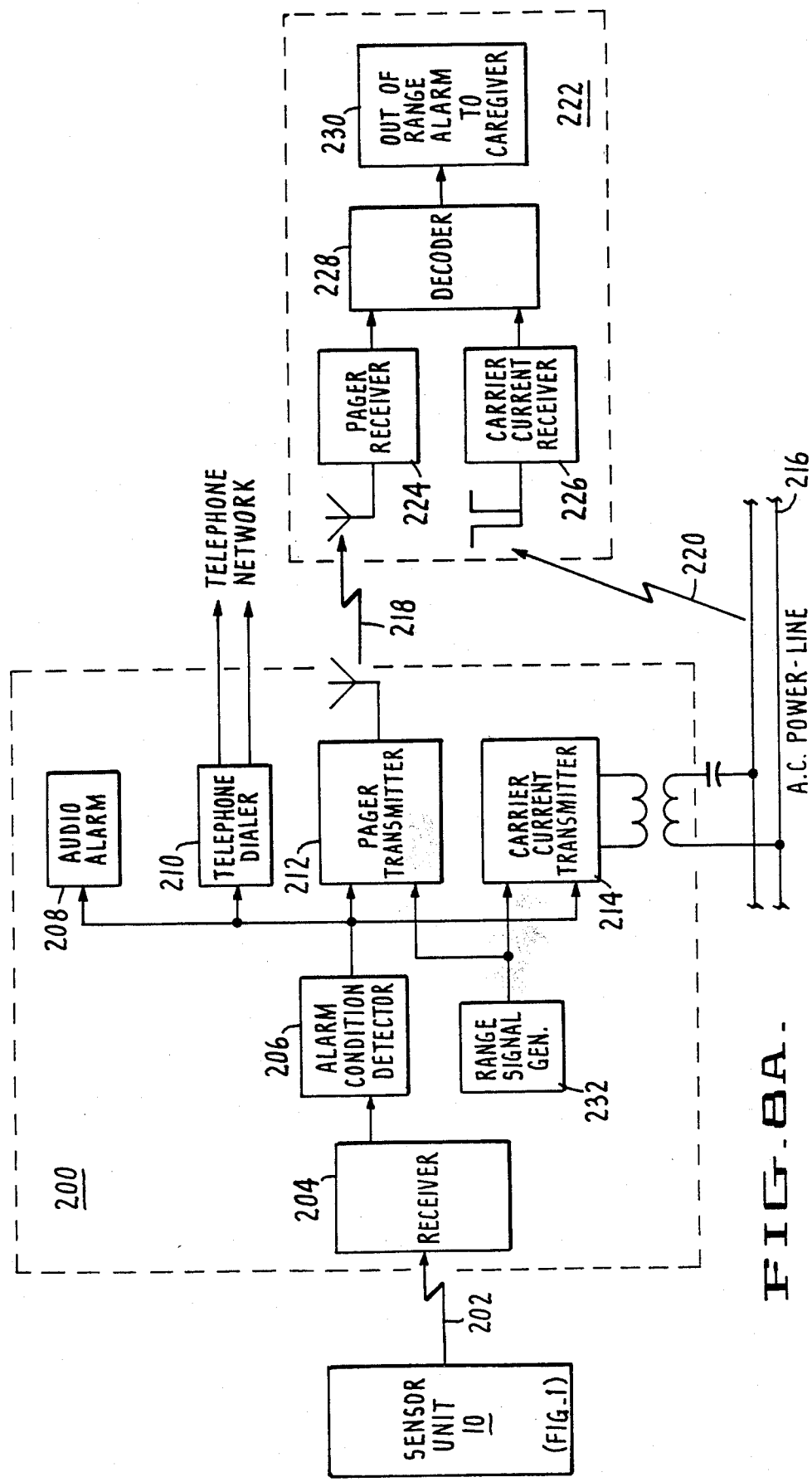

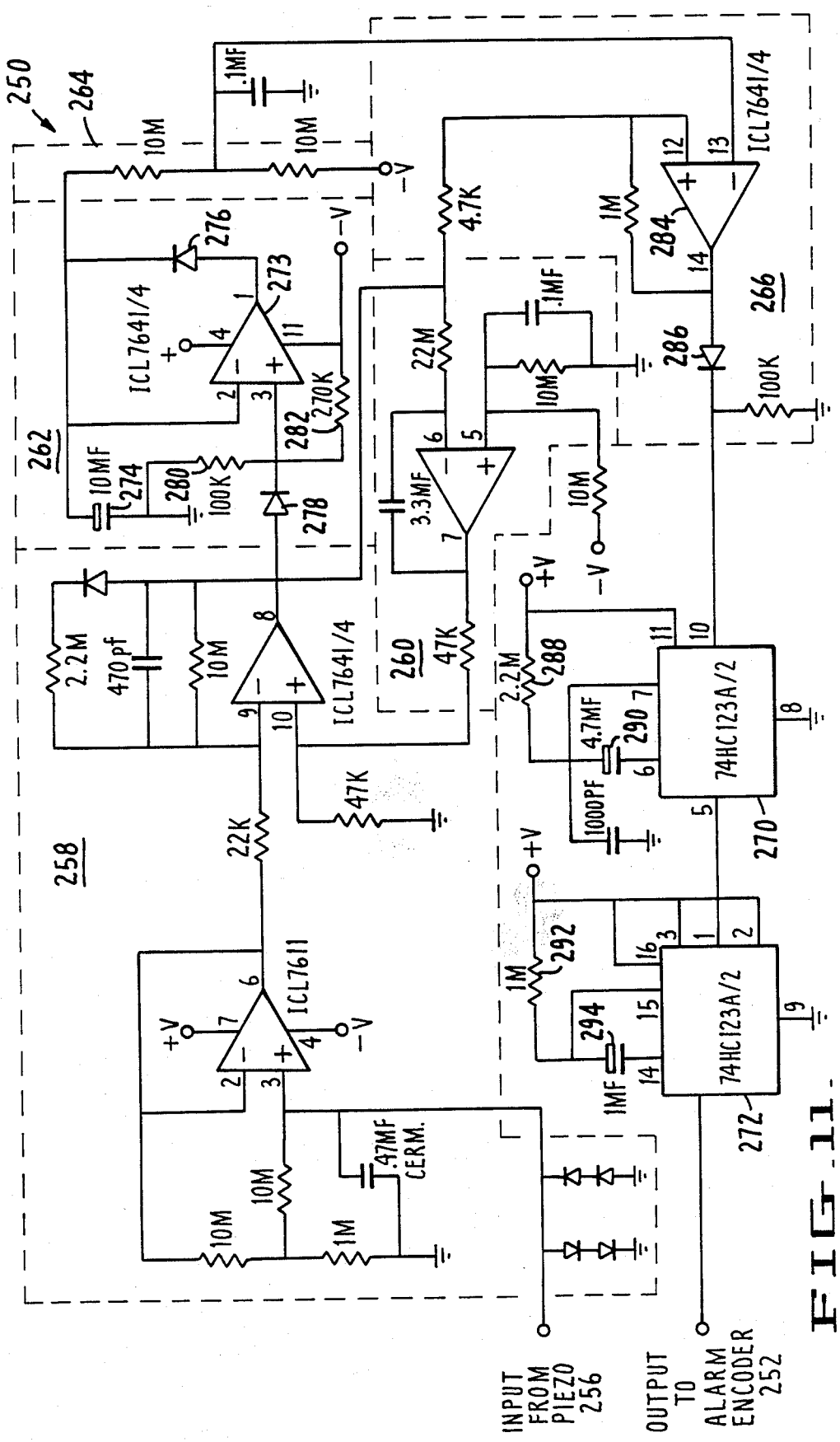

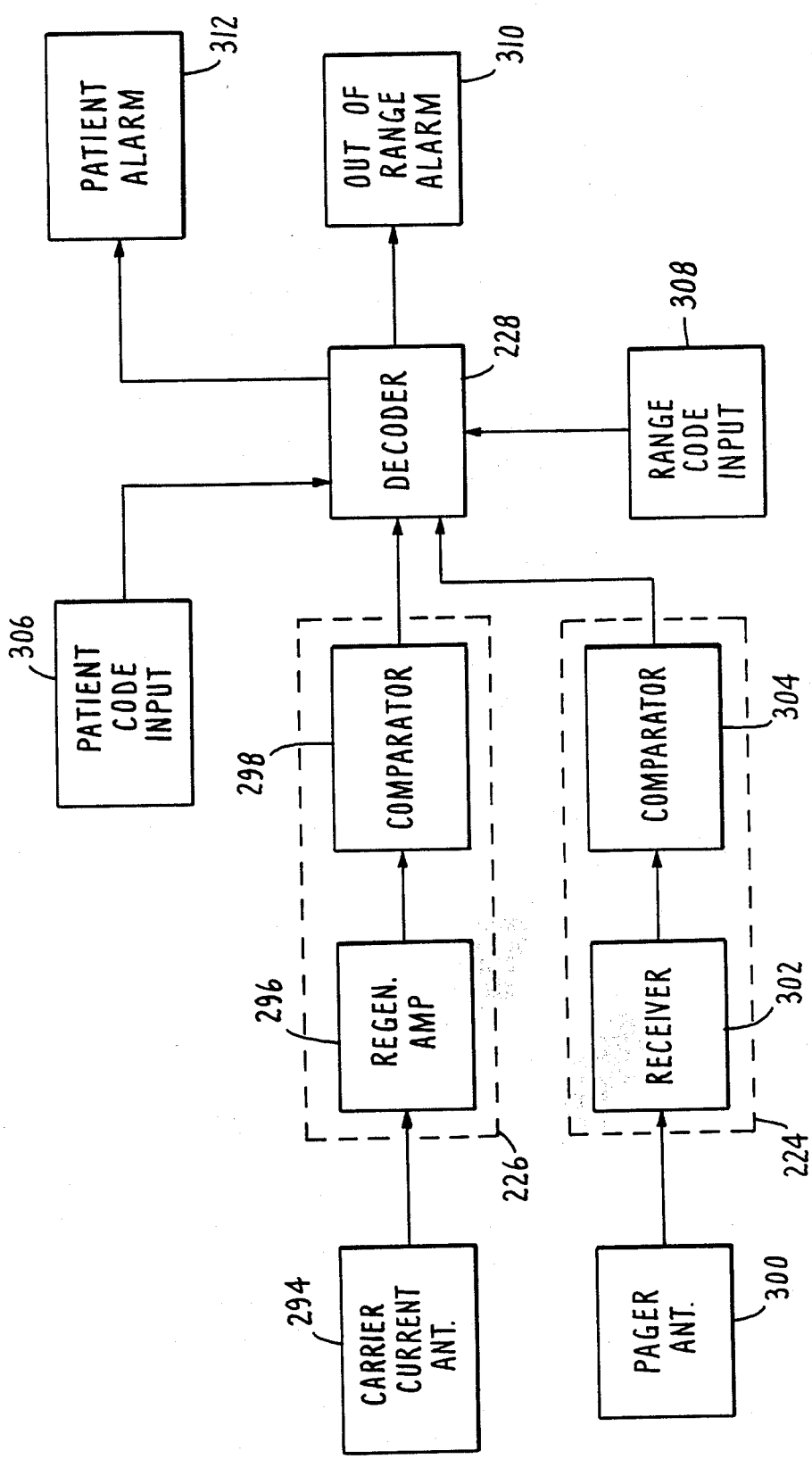

PORTABLE, MULTI-CHANNEL, PHYSIOLOGICAL DATA MONITORING SYSTEM

This a continuation-in-part of U.S. patent application Ser. No. 910,457, filed Sept. 23, 1986 now abandoned.

BACKGROUND OF THE INVENTION

1. Field of the Invention

The present invention relates to medical monitoring systems and, in particular, to a highly portable, non-invasive, physiological monitoring system for alerting a caregiver that a patient is in need of medical assistance.

2. Discussion of the Prior Art

In the medical monitoring area, multi-channel patient monitors are currently available such as those manufactured by Hewlett-Packard Company of Palo Alto, Calif. These monitors are hard-wired between the patient-worn sensors and the processing/display module. They are bulky and unsuitable for less than intensive, critical care monitoring. These bedside and console monitors offer multiparameter sensing, but are not intended to be worn directly by the patient. They do not offer a nurse paging feature, but instead require constant monitoring by an attendant.

The Hewlett-Packard devices include telemetric modules which provide ECG telemetric data. The Hewlett-Packard model 78100A/78101A are a transmitter and receiver system by which a ECG signal, derived from a set of sensors worn by the patient, is transmitted to remote monitoring equipment. The receiver in such a system is intended to be placed on a table top and not to be worn by the caregiver. Thus, the caregiver must remain in visual or audio contact with the receiver unit at all times.

A unit offered by Lifeline Systems Inc. of Watertown, Mass. include a subscriber worn help button and a receiver positioned within a 200 foot vicinity of the subscriber. When the subscriber presses the help button, the receiver makes a call on the telephone line to an emergency response center where it is acted upon. The system includes a timer which requires that the user reset it manually. In absence of such a reset, an alarm is automatically sent out indicating that the user is unable to call for help. Such a system requires user intervention and also is not capable of providing a real time alarm when the user is unable to call for help. Further, the ability of the system to get through to the emergency response center, or to a caregiver, in the event of an emergency is a function of the reliability of the telephone system. Further, even if the alarm is received and responded to, such help may not be forthcoming for several minutes which could be critical to the survival of the patient being monitored.

It would therefore be desirable to have a system which can be worn by the subject being monitored and which can provide alarm indications to caregivers in the immediate vicinity of the subject being monitored, as well as to remote caregivers, and which also is capable of detecting alarm conditions separate and apart from manual activation of the system by the subject being monitored. It would also be desirable to have a system which has redundant transmission paths to insure that caregivers are summoned in an expedient manner.

Conventional practice for diagnosing sleep disorders requires that the patient be admitted to a "sleep lab". Typically, these sleep labs are located at hospitals or clinics and consist of a special in-patient unit equipped with a complicated array of cumbersome polysomnograph equipment. The patient is required to sleep in the unit while being monitored by a combination of bulky, uncomfortable sensors which are attached to various parts of the body. Obviously, the accuracy of the data generated under these circumstances is suspect because of the unfamiliar environment and physically uncomfortable circumstances in which the data is taken.

To eliminate the problems associated with "sleep labs", solid-state portable physiological monitoring systems have been developed for use in the patient's own environment.

One such system is available from Vitalog Corporation. The Vitalog system is a portable microcomputer which monitors information from up to eight physiological sensors. This information is processed and stored in on-board, solid-state memory for subsequent retrieval or display by a separate computer system.

The Vitalog system contains an eight-channel analog-to-digital interface and an R-wave detector. The multi-channel A/D converter samples eight analog inputs. A one-channel motion sensor composed of an array of omnidirectional mercury tilt switches detects patient movement. A one-channel electrocardiogram (ECG) signal is monitored using three standard ECG electrode pads. The amplified ECG signal is connected to an A/D channel and also to the R-wave detection circuit. A temperature sensor array monitors three channels of temperature using standard probes. Either one or two channels of respiration may be monitored. One channel can be programmed to monitor a patient response button.

When the Vitalog system is activated, its ROM-based operating system continuously monitors the sensor inputs. After each programmed monitoring period, information relating to heart rate, physical activity and temperature is stored. A running mean of normal R—R intervals is calculated at the end of each heart beat. At the end of each monitoring period, the current mean is encoded into one of 16 levels (4 bits) and stored. A filtered output count from the motion sensor is accumulated and encoded into one of 8 levels (3 bits). Temperature information is encoded using a 3-bit tracking scheme.

The Vitalog system can store data from a minimum of 3600 epochs. Data compression is used to ensure that no memory is used when data is unchanging.

A fundamental shortcoming of the Vitalog system is that it lacks individual event resolution. That is, because data gathered over a full monitoring period must be stored in limited on-board memory for retrieval at the end of the monitoring period, the data must be compressed prior to storage. This requires pre-storage processing according to a predefined algorithm, further limiting the stored data characteristics to rigid identifying and modifying signatures, thus reducing analytical flexibility Thus, while the Vitalog system provides a screening tool, it does not address the need for a low cost, reliable, portable physiological data recording system which provides high data resolution for a number of parameters over long periods of time.

SUMMARY OF THE INVENTION

These an other problems and disadvantages of previous monitoring systems are overcome by the present invention of an apparatus for notifying an ambulatory caregiver of the condition of a patient, including monitoring means on the patient to monitor a physiological condition of the patient, which determine whether the caregiver should be notified, and which transmit a caregiver notification signal; base station means positioned apart from the patient which is responsive to the caregiver notification signal for relaying the caregiver notification signal over a plurality of redundant but independent transmission paths; and means positioned on the caregiver which are responsive to the caregiver notification signal as transmitted by the base station means for providing a predetermined indication to the caregiver that a caregiver notification has been received.

In the preferred embodiment of the present invention the monitoring means positioned on the patient normally operate in a low power condition until an alarm condition is sensed. This permits the use of batteries as a power source. When an alarm condition is sensed, the monitoring means switches to a transmission mode in which substantially all of the available power is directed towards transmitting the caregiver notification signal. In the preferred embodiment of the present invention the plurality of redundant but independent transmission paths can include the use of carrier current transmitters which utilize the AC power line for a localized radio link, and also the use of a pager type radio link.

It is envisioned that both the monitoring means positioned on the patient and the receiver means positioned on the caregiver would be preferably battery powered. In order to ensure long battery life, a low power means for determining an alarm condition is desirable. Accordingly, it is another aspect of the present invention that an analog, adaptive threshold detector is provided which operates in a low power mode when a non-alarm condition is present, and which initiates an alarm mode, which transmits at high power, when an alarm condition is encountered. The adaptive threshold detector includes an analog memory, an analog divider, a comparator, a retriggerable oneshot, and an output oneshot. The analog memory, the divider, and the comparator are used to compare two successive periods in a waveform which corresponds to the physiological parameter being monitored. The comparator determines whether the later period has a signal magnitude which is at least a predetermined percentage of the signal magnitude for the earlier period. As long as that condition exists the output oneshot and retriggerable oneshot are maintained in a non-alarm condition.

In the present invention, the means for determining when an alarm condition exists can be located at either the base station or in the device worn by the patient. In one embodiment of the present invention, the alarm condition determining means are located in the device worn by the patient and a simplified physiological parameter sensing scheme is used. As a result, this embodiment of the present invention is suitable for non-clinical or non-hospital settings.

Another feature of the present invention is range circuitry which alerts the caregiver when the caregiver or patient is out of range, and which alerts the patient when the patient is out of range of the system.

It is therefore an object of the present invention to provide a monitoring and alarm generating system which utilizes a plurality of redundant telemetry paths for notifying a caregiver of the need for medical and other attention for the patient being monitored.

It is another object of the present invention to provide a patient monitoring and alarm generating system which includes a device worn by the patient which senses physiological parameters, determines when an alarm condition exists and transmits an alarm to a base station, and wherein the base station transmits an alarm to the caregiver via redundant, independent telemetry channels.

It is still another object of the present invention to provide a patient monitoring and alarm generating apparatus which includes means for determining and alerting the caregiver when either the caregiver or patient is out of range of the base station.

These and other objectives feature and advantages of the present will be more readily understood upon consideration of the following detailed description of the preferred embodiments of the present invention and the accompanying drawings.

BRIEF DESCRIPTION OF THE DRAWINGS

FIG. 8A is a simplified block diagram of one of the embodiments patient monitoring/alarm generating embodiment to the present invention, wherein the alarm condition detection is found in the base station.

FIG. 11 is a detailed schematic of the alarm condition detector of FIG. 10.

FIG. 12 is a simplified block diagram of the device worn by the caregiver in accordance with the present invention.

DETAILED DESCRIPTION OF A PREFERRED EMBODIMENT

Figure 1:
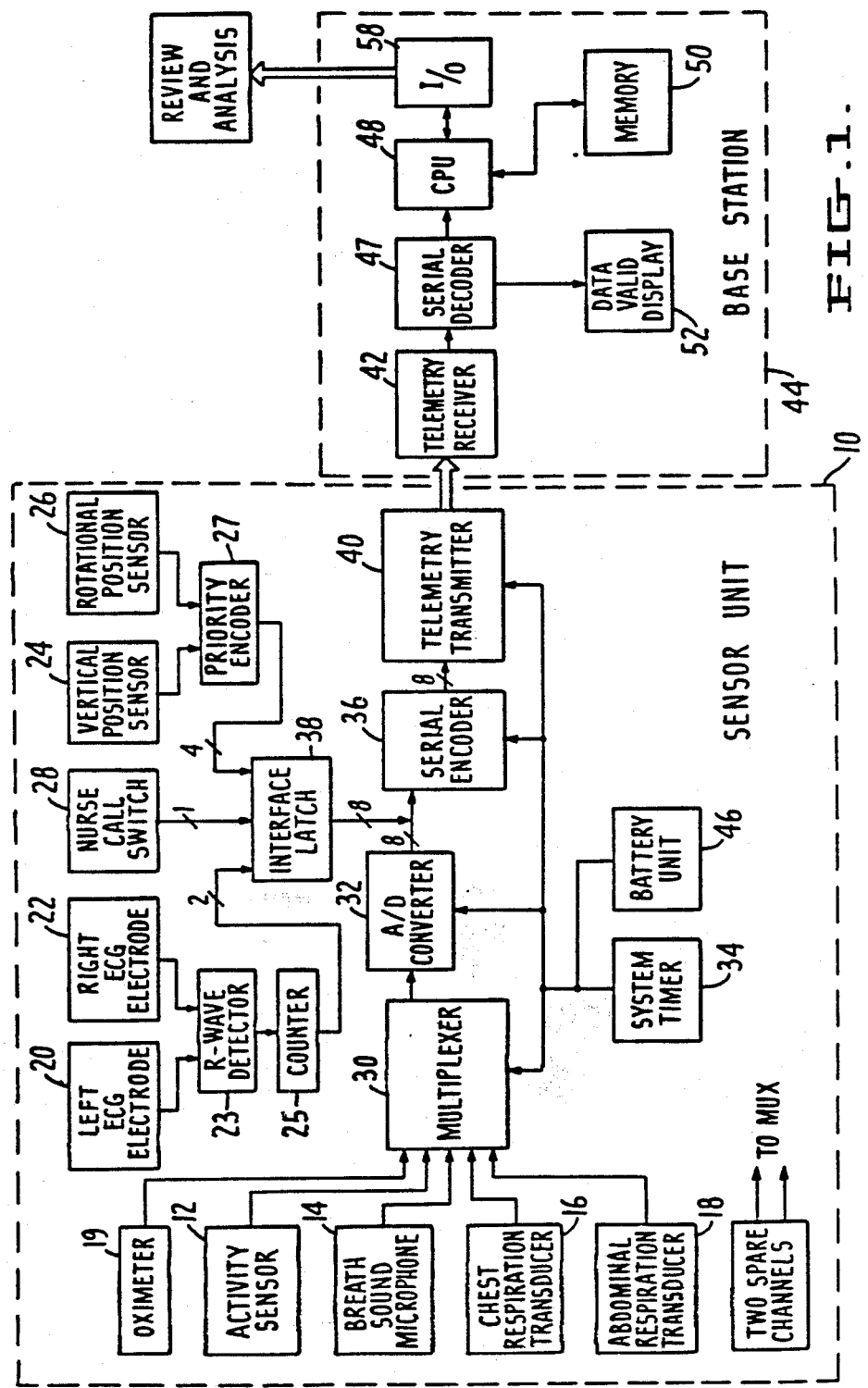
FIG. 1 is a schematic block diagram illustrating the system of the present invention.

FIG. 1 shows a schematic block diagram of the monitoring system of the present invention.

A portable sensor unit 10, which is worn by the patient to be monitored, includes a number of sensors which continuously gather physiological data from the patient and generate corresponding electrical signals.

In the embodiment shown in FIG. 1, the physiologic data sensors include: an activity sensor 12, a breath-sound microphone 14, a chest respiration transducer 16, an abdominal respiration transducer 18, an oximeter 19, left and right electrocardiogram (ECG) electrodes 20 and 22, respectively, a vertical position sensor 24 and a rotational movement sensor 26. The sensor unit 10 also includes a manually operated, nurse call switch 28. The embodiment of the invention described herein also includes two spare sensor channels which could be used to monitor additional physiological parameters, but are presently used to provide warning signals indicating low battery power and an ECG "leads-off" condition, as described below.

The electrical signals generated by activity sensor 12, breath-sound microphone 14, the two respiration sensors 16 and 18 and oximeter 19 are analog signals which are provided to a multiplexer 30. Multiplexer 30 sequentially forwards these signals, together with the signals from the two spare channels, to an analog-to-digital converter 32 in response to clock signals provided by a system timer 34. The A/D converter 32 converts the analog input signal from the sensors to a binary data word which serves as the input to a serial encoder 36.

The signals from the left and right ECG electrodes 20 and 22 are provided to an ECG and R-wave detector 23. The output of R-wave detector 23, which is representative of the patient's heart beat rate, is provided to a counter 25 which generates a 2-bit heart beat signal to interface latch 38. The signals from vertical position sensor 24 and rotational movement sensor 26 are provided to a priority encoder 27 which provides a 4-bit signal representative of these parameters to interface latch 38, the signal from the vertical position sensor 24 being given priority. Nurse call switch 28 provides a 1-bit "on-off" signal to latch 38.

The 8-bit output of interface latch 38 comprises 7 bits of data from its just-described associated sensors and an additional system synchronization bit, set to 1, to inform the base station 44 of the beginning of a transmission sequence. The 8-bit output of A/D converter 32 also includes 7 data bits from its associated channels, the eighth bit being always set to zero to distinguish it from the synchronization bit of the interface latch output.

Serial encoder 36 converts each of the 8-bit parallel digital signals from A/D converter 32 and interface latch 38 to a serial data stream. The serial data stream is then provided to a digital telemetry transmitter 40 which transmits the uncompressed data by low-power radio signals at one-half second intervals to a telemetry receiver 42 of portable base station 44.

Thus, the complete transmission sequence is composed of eight channels, each 8 data bits wide, as described above. Each channel is composed of 12 synchronization pulses, a 7-bit address which identifies the channel and the 8 data bits.

The power for the sensor unit 10 is provided by a battery unit 46, which comprises four AAAA size batteries of 0.3" thickness. Use of these "quad-A' batteries allows the thickness of sensor unit 10 to be less than about 0.5 inches, making it relatively inobtrusive in comparison to prior art devices.

The radio signal received by telemetry receiver 42 is provided as a digital signal to CPU 48 which stores the data in memory 50 and/or communicates with additional peripheral devices via I/O port 58 for review and analysis of the data. The base station 44 also includes an LED display which verifies that data is being received and stored.

Figure 2:
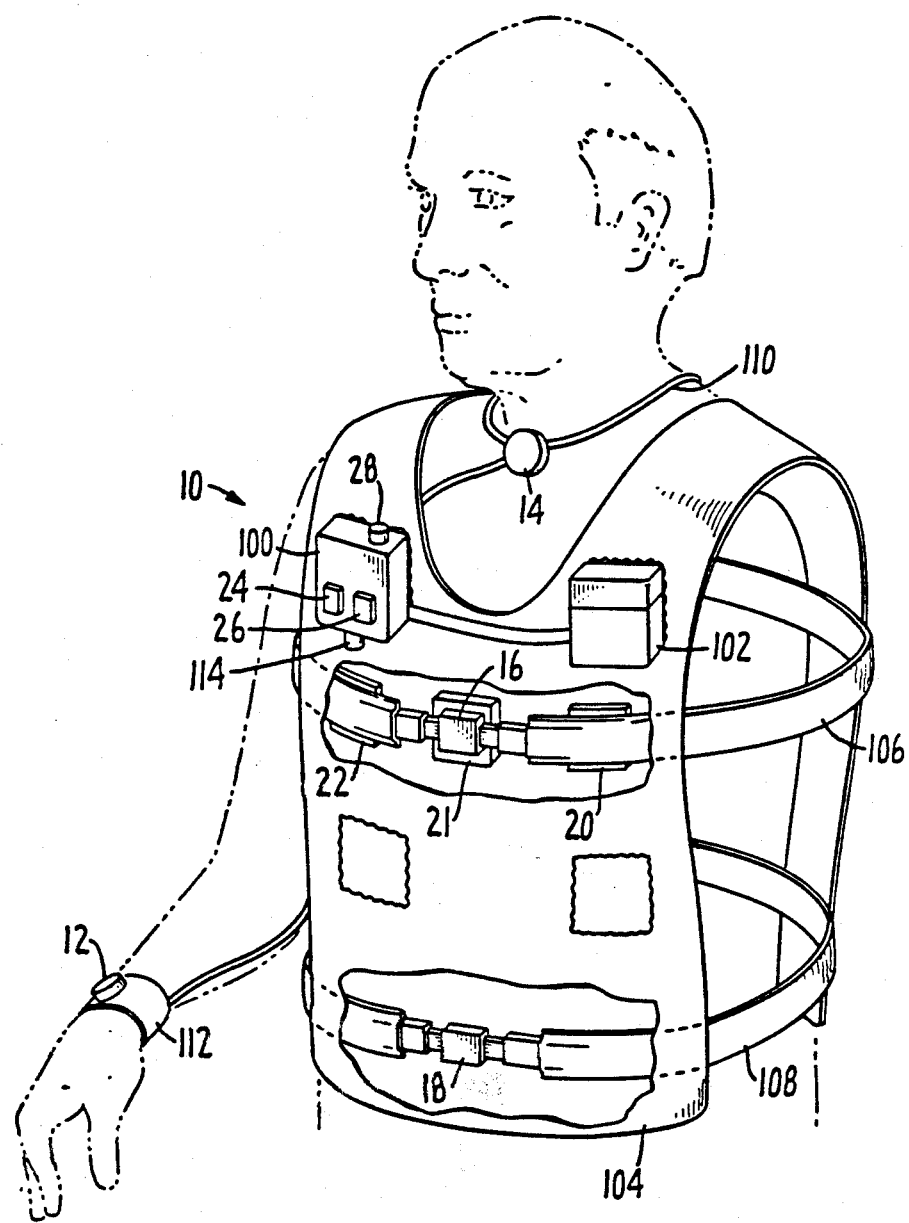
FIG. 2 is an illustration of the sensor unit of the system of the present invention.

As shown in FIG. 2, sensor unit 10 includes a hybrid analog/digital circuit pack 100 which receives signals from the various sensors described above and provides these signals as a serial digital data stream to a second pack 102 which includes battery unit 46 and telemetry transmitter 40.

The circuit pack 100 and the battery/transmitter pack 102 are both attached to a body vest 104 by means of a Velcro ® fastener patch attached to the back of each unit 100, 102 and a corresponding patch attached to the vest 104. The vest 104 includes Velcro ® fastener patches for this purpose located both at the upper chest portion and at the abdominal portion so that the patient may attach the two packs 100 and 102 at the personally most comfortable location.

The hybrid circuit pack 100 receives the two respiration signals from two conventional respiration transducers 16 and 18 which are mounted around the patient's chest and abdomen, respectively. As shown in FIG. 2, each of the chest and abdominal respiration transducers 16 and 18 is formed as part of a body strap 106 and 108, respectively, which fits around the patient's torso to position the transducer at the desired location.

Two ECG electrodes 20 and 22 are attached to the patient, one at each side of the patient's chest area, and connected by shielded leads to the hybrid circuit pack 100. A third ground ECG electrode 21 is attached to the patient between the other two. In the preferred embodiment, the three ECG electrodes 20, 21 and 22 are connected to the inner side of chest respiration strap 106.

An electric microphone 14 is located at the patient's suprasternal notch by means of a throat collar 110. Microphone 14 monitors the patient's breath sound and transmits a representative signal to the hybrid circuit pack 100.

A vibration piezo transducer 12 mounted on the patient's wrist by means of a bracelet 112 also provides its signal to the hybrid circuit pack 100.

The hybrid pack 100 further includes two position sensors 24 and 26 which, in the preferred embodiment, are mercury switches which monitor rotational movement and vertical position, respectively. A position switch 114 mounted at the bottom of the hybrid circuit box is used to normalize the body position of the patient when the position switch 114 is pressed. That is, when the position switch 114 is pressed, the patient's position at that time is defined as being "nose up", i.e., the patent is on his back with his nose in the vertical position. A nurse call button 28 is located at the top of the hybrid circuit pack 100 and may be activated by the patient.

Figure 3A:
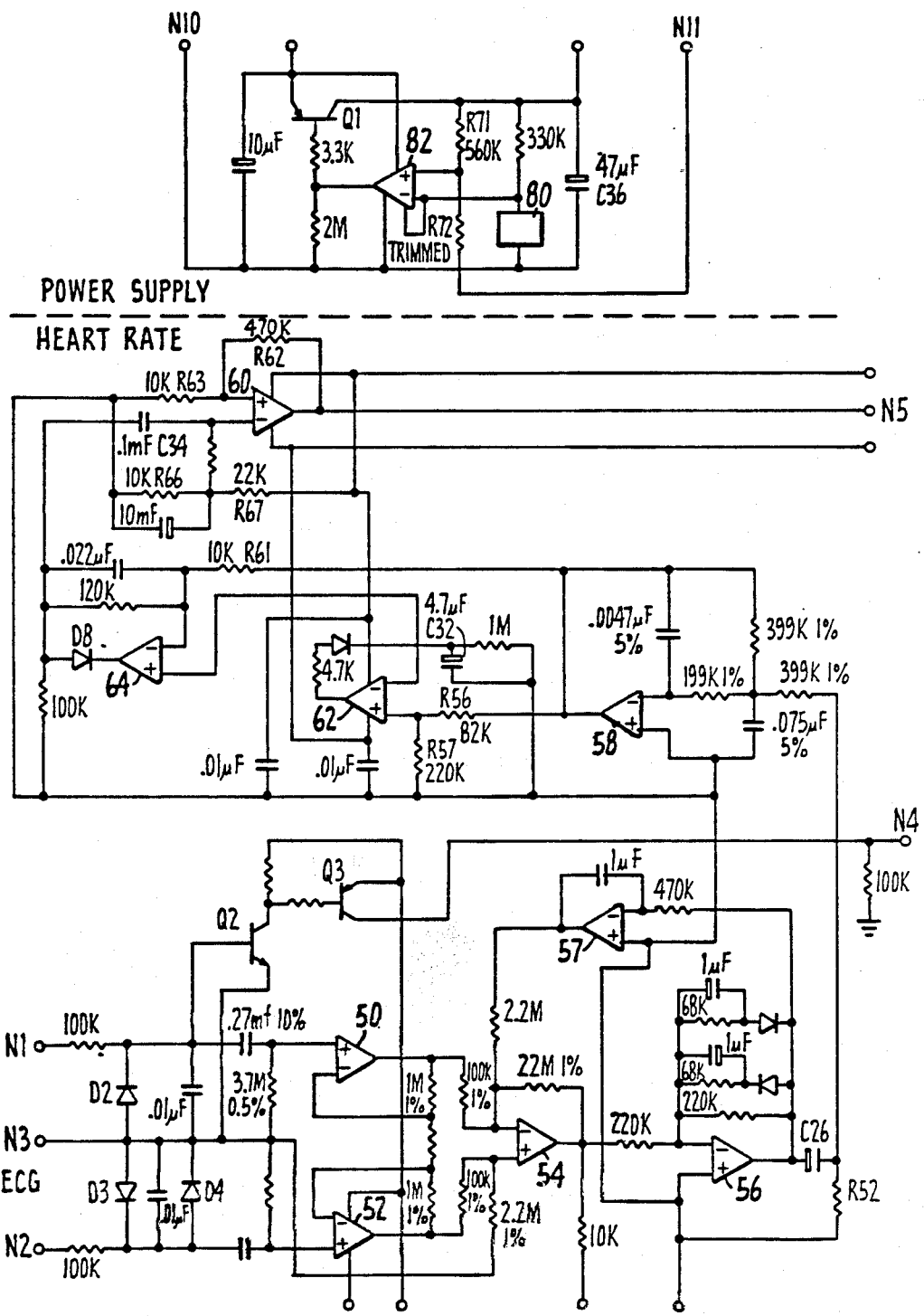
FIGS. 3A and 3B combine to provide a schematic circuit diagram illustrating the analog portion of the sensor unit circuit of the system of the present invention.
Figure 3B:
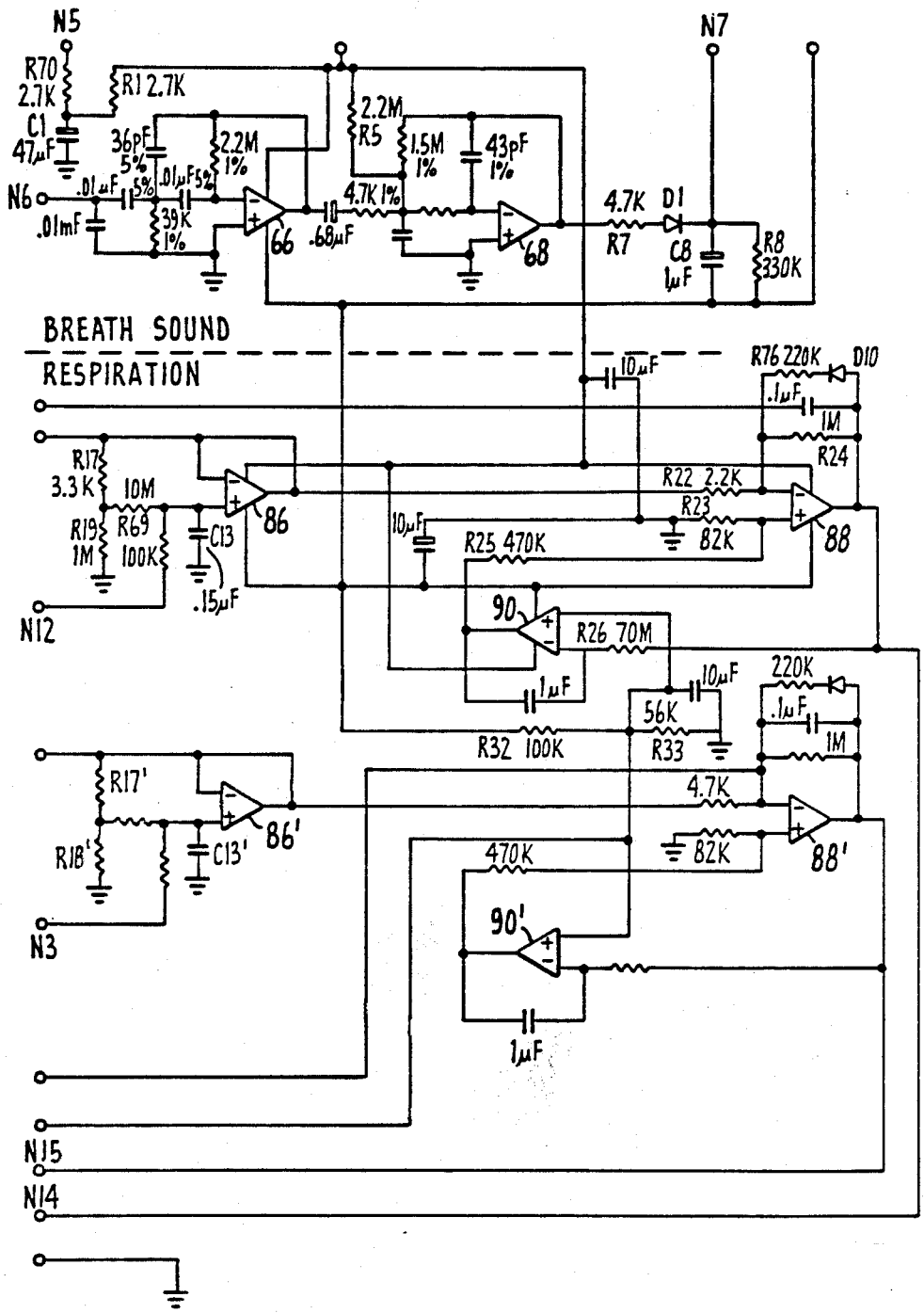

FIGS. 3A and 3B provide a detailed circuit schematic diagram of the analog portion of sensor unit 10.

As shown in FIG. 3A, nodes N1 and N2 receive the left and right ECG signals, respectively, from left and right ECG electrodes 20 and 22 for the Heart Rate portion of the circuit. Node N3 is connected to center ECG/ground electrode 21. The ECG inputs from nodes N1 and N2 are provided to components 50 and 52, respectively, which together with component 54 form an instrumentation amplifier with a gain of approximately 1000. Transistors 22 and Q3 form a "leads-off" detector circuit, where the base/emitter junction of transistor Q2 forms a fourth diode with clamping diodes D2, D3 and D4. This "leads-off" detector circuit operates with an external bias such that the conducting path is either from node N1 to ground node N3 or from node N1 to node N2 with the ECG leads connected. With the leads off, the current from ECG electrode 20 which is connected to node N1, is provided to the base of transistor Q2. This turns on both transistor Q2 and transistor Q3 and provides a high level output at node N4. This output is provided to one of the unused transmission channels, as mentioned above, to indicate that an ECG lead is disconnected.

A gain block composed of instrumentation amplifier 56, together with its feedback component, form a limiting amplifier with amplitude and slew rate limiting. The output of instrumentation amplifier 56 is zeroed by an autonull amplifier 57 which assures that the output of instrumentation amplifier 56 is forced quiescently toward zero. The output of instrumentation amplifier 56 is provided to a high pass formed by capacitor C26 and resistor R52 and also to a band pass filter 58. The output of band pass filter 58 is provided to a resistor divider formed by resistors R56 and R57 to ground and also to resistor R61 which is an input of amplifier 64. Amplifier 62 and its feedback circuitry receive the information from the output of amplifier 58 and capture that peak voltage onto capacitor C32. The voltage of capacitor C32 is then applied to the positive input of amplifier 64, the other input to amplifier 64 being provided through previously-mentioned resistor R61. The output of amplifier 64 through polarity blocking diode D8 forms a negative going waveform, which is the difference between the peak voltage applied at the positive input to amplifier 64 and the output of amplifier 58, and is applied through capacitor C34 to a comparator 60, the threshold of which is set by a divider provided by resistor R67 through resistor R66 to ground. Resistors R62 and R63 form positive feedback, or hysteresis, to assure clean switching of the output. The output of comparator 60 is then provided to node N5 which is the output pin of the Heart Rate, or ECG, circuit and the input to heart rate counter 25 shown in FIG. 1. The total of this aforedescribed circuitry forms R-wave detector 23 which provides one pulse per peak electrical QRS complex.

Referring now to the Breath Sound section of FIG. 3B, resistor R1, capacitor C1 and resistor R70 form a bypass and bias network for electret microphone 14, the network then being connected back to node N6 of the circuit. The network around amplifier 66 forms a gain block and band pass filter which feeds a second gain block and band pass filter 68. The band pass of this network is approximately 300-900 Hz, while the network gain is approximately 500. The output of filter 68 is biased by resistor R5 toward the negative rail to allow full scale presentation of the breath sound signal amplitude. This output is applied to resistor R7 and through diode D1. The peak waveform is captured across capacitor C8 to the negative rail with the discharge path through resistor R8 and parallel with capacitor C8 to output node N7 which is an input to multiplexer 30.

Figure 4:
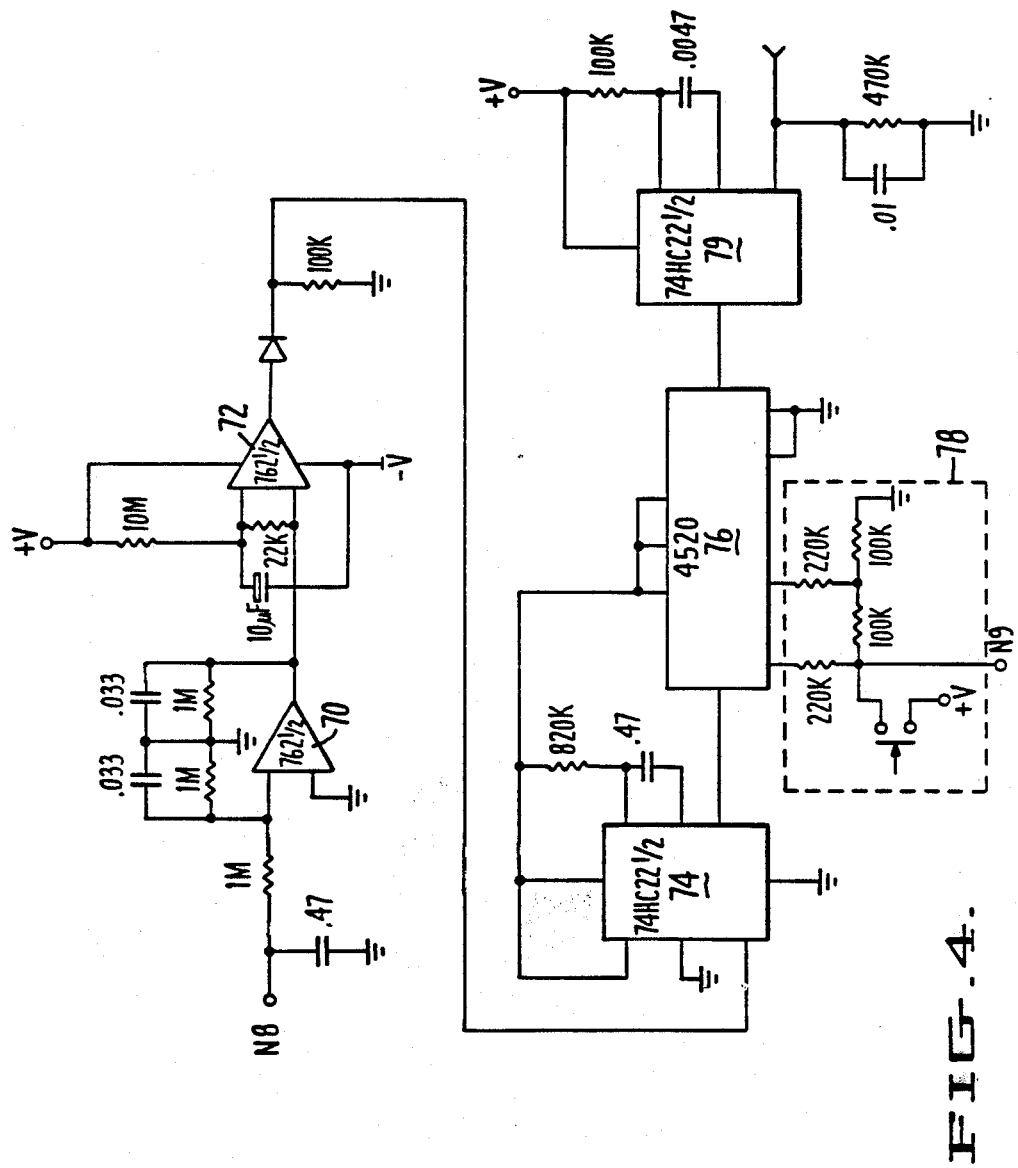
FIG. 4 is a schematic circuit diagram illustrating the activity sensor portion of the sensing unit circuit of the system of the present invention.

Referring now to FIG. 4, which shows the Activity portion of the circuit, the signal from the activity transducer 12 is received at node N8, provided to amplifier and low pass filter 70 and then to tracking comparator 72. The output of tracking comparator 72 is provided to non-retriggerable one-shot 74 which clocks out a digital signal to counter 76. The output of counter 76 is provided to a digital-to-analog converter 78, the output node N9 of which serves as an input to multiplexer 30. The counter 76 is reset to the 0 position by non-retriggerable one-shot 79 which is triggered by the falling edge of the transmitter enable signal, as described below.

Referring now to the Power Supply section of FIG. 3A, a 1.2 reference voltage 80 is provided to the negative input of amplifier 82. Transistor Q1, which is a series pass element, is operated in the inverted mode for low dropout characteristic. The feedback path for the regulator is through resistors R71 and R72 where nodes N10 and N11 are tied together for this application. Capacitor C36 forms an output compensation network to provide stability, since transistor Q1 is operating as a gain stage. Resistor R15 provides start-up current for the regulator.

Referring now to the Respiration section of FIG. 3B, the signals from both the abdominal and the chest transducers 18 and 16 are received at nodes N12 and N13, respectively. The signal received at node N12 is applied to capacitor C13 and to a boot strap amplifier 86 formed by booting resistors R17 and R19 to ground, where resistor R69 is brought off the center of this bootstrap configuration and provides a thousand megohm equivalent input impedance. The output of bootstrap amplifier 86 is applied through a gain block 88, the gain of which is set by resistors R22 and R24. The output of amplifier 88 is provided past one diode drop and again is reduced by the forward conductivity of diode D10, putting resistor R76 in parallel with resistor R24. Amplifier 90 and its associated circuitry provide an autonull loop for the output of bootstrap amplifier 88 which is sensed through resistor 26. The output of amplifier 90 is coupled back into amplifier 88 through resistor R25. The quiescent voltage of amplifier 88 is set by resistor divider R32 and R33 and is approximately −1.1 volts. Thus, the output of the abdominal transducer portion of the circuit is provided at node N14.

The chest transducer signal received at node N13 is similarly processed via amplifiers 86′, 88′ and 90′ to provide a chest transducer output at node N15.

Figure 5A:
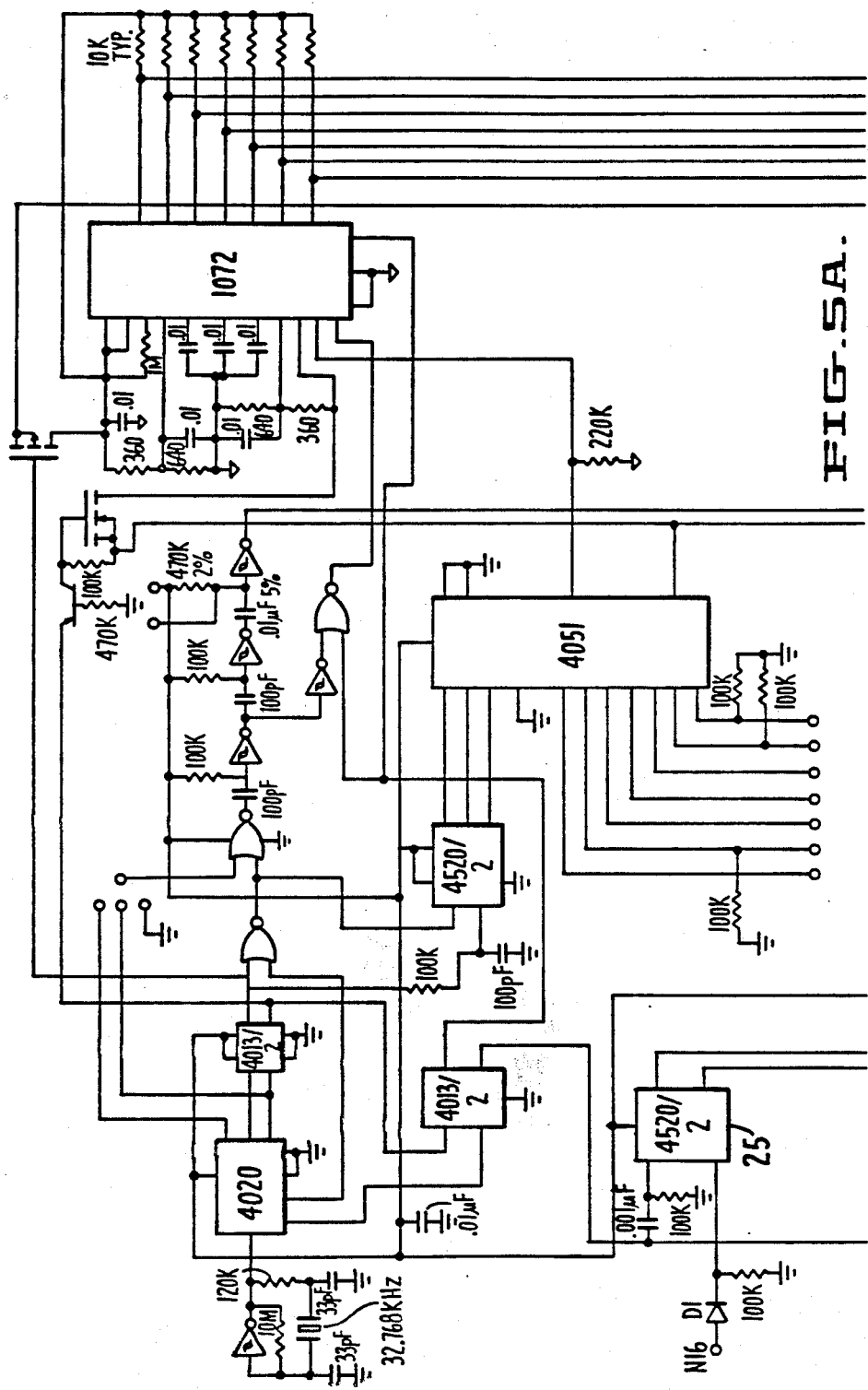
FIGS. 5A and 5B combine to provide is a schematic circuit diagram illustrating the digital portion of the sensing unit circuit of the system of the present invention.
Figure 5B:
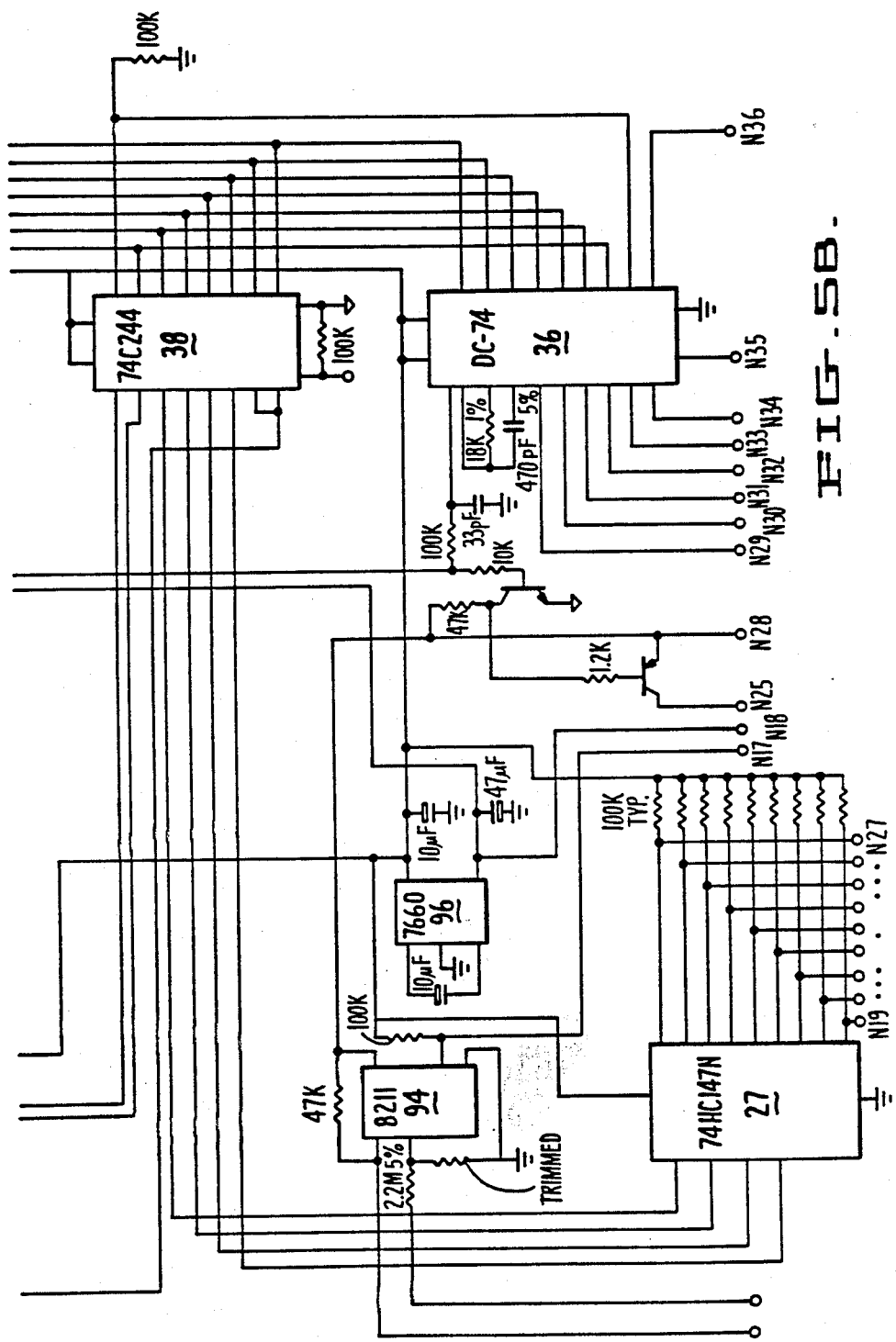

Referring now to the digital portion of the sensor unit circuitry shown in FIGS. 5A and 5B, the output of the Heart Rate circuitry of FIG. 3A is provided to node N16 and passes through diode D1 which shifts the level from positive to negative voltage. The logic requires only a positive to ground; therefore, diode D1 blocks the negative voltage and 4-bit counter 25 stores the heart rate count. This information is then provided to interface latch 38 as a 2-bit signal every one-half second during transmission.

A low voltage battery detector 94 provides its output on node N17 to one of the otherwise unused analog channels mentioned above. A low battery is, therefore, detected at base station 44.

A voltage converter 96 receives the voltage from the battery unit 46 and converts it to a negative voltage output. Therefore, node N18 of the digital hybrid circuit is the −4.5 voltage negative power supply point for the system.

Priority encoder 27 receives the signals from both position sensors 24 and 26, with the vertical position transducer receiving highest priority, and encodes it into four bits of binary weighted code. Nodes N19–N27 are the input pins from the position transducers.

Node N28 of the digital hybrid circuit switches the transmitter power supply and is gated from the output of the system enable timer 34. Thus, the signal at node N28 resets the one-shot 79 of the activity circuit.

Serial encoder 36 receives parallel digital data presented on its input pins and applies a serial output to the channel address at nodes 29–35, bringing these nodes either to ground or to the positive rail. Serial encoder 36 also produces an 8-bit serial data stream at node N36 which modulates transmitter 40.

Interface latch 38 switches in the digital information from its associated sensors during the digital channel transmission.

A/D converter 32 receives the output of analog multiplexer 30 and, upon command, digitizes each of the analog levels presented by multiplexer 30.

Transistors Q4 and Q5 are gated power supply devices which provide power to A/D converter 32.

Figure 6:
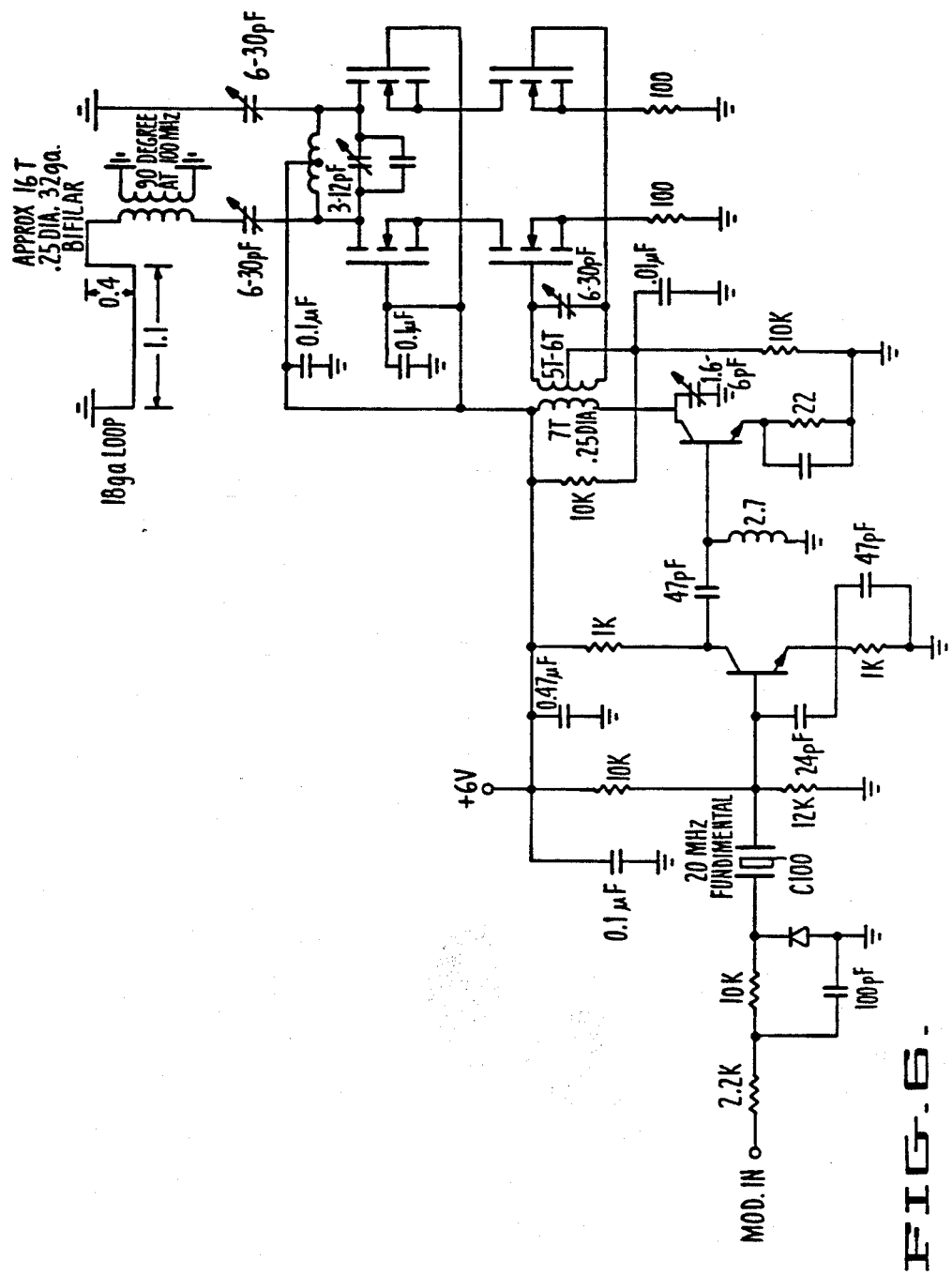
FIG. 6 is a schematic diagram illustrating the circuitry of the telemetry transmitter used in the system of the present invention.

FIG. 6 shows a detailed schematic circuit diagram of the digital telemetry transmitter 40.

As shown in FIG. 6, the serial data transmissions from encoder 36 are first modulated by a programmable data coder and then provided to a low pass filter. The filtered signals are then provided to a modulator, the output of which is forwarded to an oscillating section of the transmitter circuitry, the frequency determining element of which, i.e., crystal C100, has a resonant frequency of approximately 20 MHz. The outputs of the crystal C100 are amplified before exiting the oscillator section of the circuit and then forwarded to a first frequency tripler which triples the third harmonic of the oscillator output. The output of the first frequency tripler section is provided to a second frequency tripler section which generates the ninth harmonic of the oscillator output. The frequency of the output of the second tripler section is in the range of 180–212 MHz, which is known as the medical band. The outputs of the second tripler section are forwarded to the antenna elements of the transmitter 40 for transmission to the base station 44.

Figure 7:
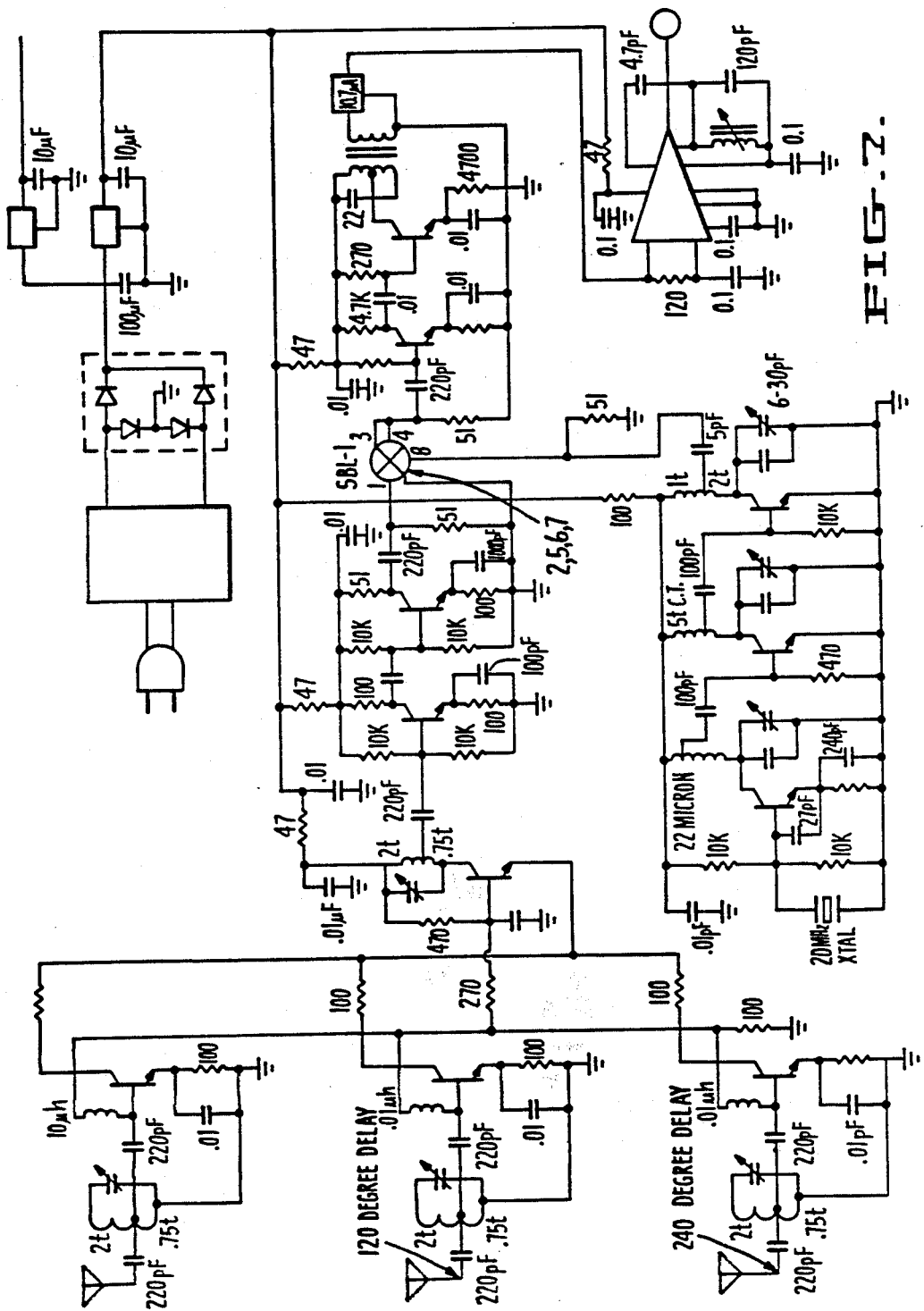
FIG. 7 is a schematic diagram illustrating the circuitry of the telemetry receiver used in the system of the present invention.

FIG. 7 shows a detailed schematic circuit diagram of the digital telemetry receiver 42. The signals transmitted from the transmitter 40 are received by the antenna elements of receiver unit 42. The signals received by the antenna elements are forwarded to an amplifier and summer network. The outputs of this network are forwarded to an RF amplifier, a mixer, and an amplifier and filter section. The output of the amplifier and filter section is provided to a serial decoder 47 which outputs an 8-bit digitized audio signal that is provided to CPU 48 for either storage in memory 50 or transmission through I/O port 58 to diagnostic equipment for analysis and review.

In the preferred embodiment, CPU 48 is an Hitachi 64180 microprocessor which directly addresses 512K of RAM and has a built-in R232C I/O port.

Data valid display 52 is an LED which is driven from a one-shot which is triggered by the data-valid port of serial decoder 47.

Referring now to FIG. 8A, one of the embodiments of the present invention will now be discussed. The embodiment of FIG. 8A employs the sensor unit 10 discussed in connection with FIG. 1, and a modified version of the base station 44, also discussed in connection with FIG. 1. It will be recalled that the sensor unit 10 is worn by the subject being monitored and provides signals from physiological sensors worn by the subject being monitored. The signals from the sensors are then transmitted to the base station for processing.

In the embodiment of FIG. 8A, a base station 200 is employed which provides analysis of the sensor signals, and redundant-path notification of the caregiver. More specifically, the telemetry signal 202 from the sensor unit 10 is received and decoded by receiver 204. Receiver 204 can be telemetry receiver 42 and serial decoder 47 of FIG. 1.

The decoded signals are then evaluated by alarm condition detector circuitry 206. Alarm condition detector circuitry 206 can be implemented in a manner similar to that described in copending U.S. patent application Ser. No. 911,101, entitled PHYSIOLOGICAL DATA ANALYSIS METHOD AND APPARATUS, filed Sept. 23, 1987, and assigned to the assignee of the present application. With such an implementation, an alarm condition could be defined as occurring when the parameters being monitored fall outside of a predetermined range for more than a predetermined number of samples. The above referenced application is hereby incorporated by reference.

Alternatively, the alarm condition detector circuitry 206 can be implemented in analog form, such as an adaptive threshold detector. One embodiment of such an analog adaptive threshold detector is shown in FIG. 11, and will be described in greater detail hereinbelow.

Upon the detection of an alarm condition, alarm condition detector circuitry 206 issues an alarm condition signal to a multiplicity of signalling devices, including: an audio alarm generator 208, a telephone dialer 210, a pager transmitter 212, and a carrier current transmitter 214. In turn these signaling devices alert a multiplicity of entities including: the subject being monitored, caregivers within a localized area, and caregivers who are off-site.

The audio alarm 208 sounds to alert the subject being monitored and any caregiver within earshot of the base station 200. The telephone dialer 210 is a conventional unit and can be programmed so that, when activated by the alarm condition signal, a paramedic or other service can be dialed up and provided with a prerecorded message as to the location, name of subject, and nature of the alarm.

The pager transmitter 212 and carrier current transmitter 214 provide redundant but independent signalling paths to the local caregiver. The pager transmitter 212 is conventional and of the pocket pager type. The carrier current transmitter is utilized to inject a radio frequency type signal into the alternating current wiring 216 of the building within which the base station 200 is located. As such, the wiring 216 is used as a localized transmitting antenna.

The local caregiver wears a receiving device 222 which receives the alarm condition signals over the pager and carrier current paths, 218 and 220, respectively, and which notifies the caregiver of an alarm condition. The receiving device includes a conventional pager receiver 224, a receiver 226 for receiving the localized transmission from the carrier current transmitter 214, a decoder 228, and a signalling device 230. Receiver 226 can be of the conventional super-regenerative type. Decoder 228 decodes the signals received from the base station 200 and provides to signalling 230 the appropriate signal to sound an alarm to the caregiver.

Also included in the embodiment of FIG. 8A is a range signal generator 232 which is located at the base station 200, and which provides a periodic signal to the caregiver receiver unit 222 via the pager transmitter 212 and the carrier current transmitter 214. The decoder circuitry 218 on board the caregiver receiver unit 222 determines when there is an absence of the periodic signal from the base station 200 and interprets this absence as an indication that the caregiver is out of range of the base station 200. The decoder circuitry 218 then enables the signalling circuit 230 to issue an out of range alarm.

In the above manner, a reliable patient monitoring system is provided.

Figure 8B:
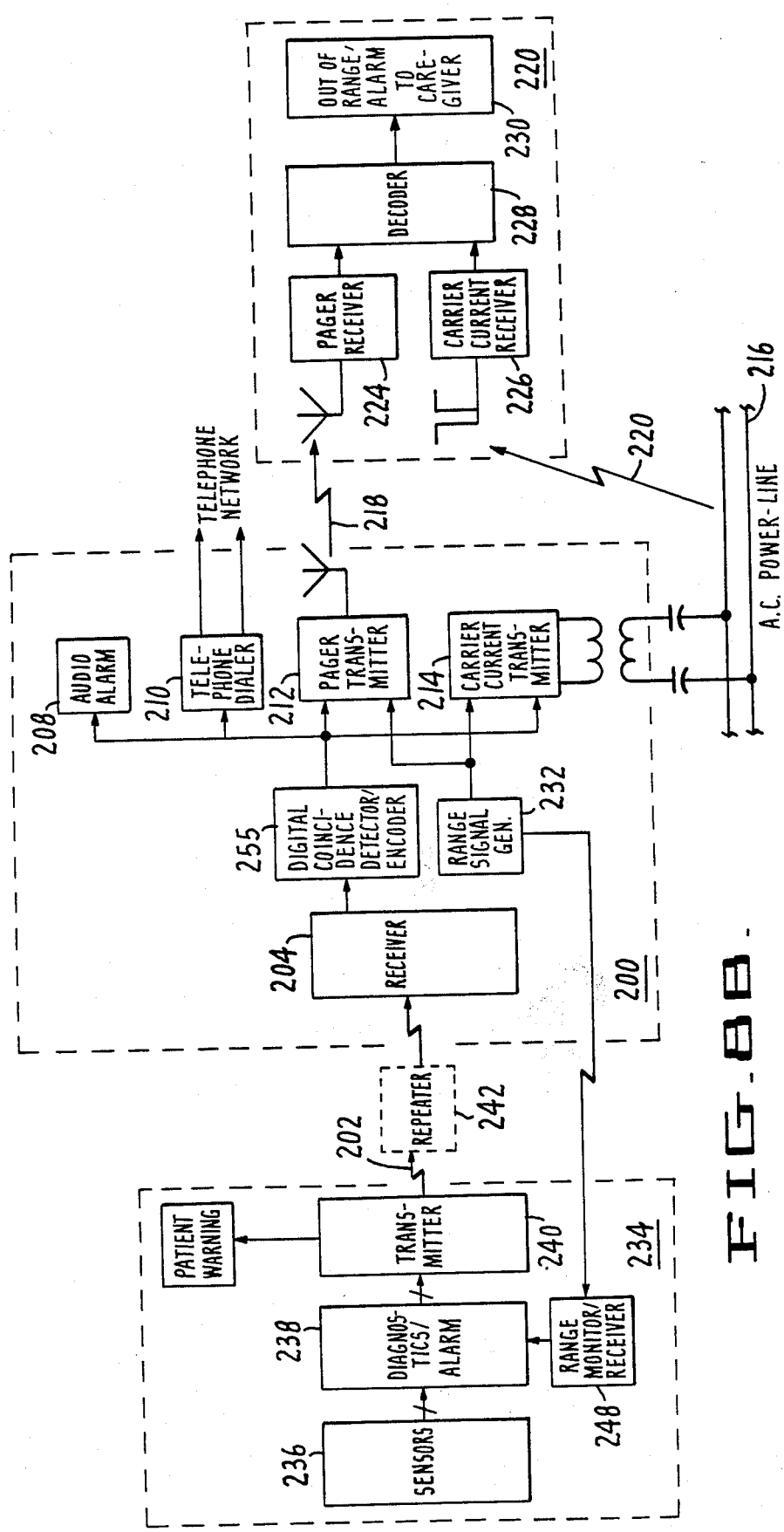
FIG. 8B is a simplified block diagram of another embodiment of the present invention wherein the alarm condition detection is found in the unit worn by the patient.

Referring now to FIG. 8B, an embodiment of the present invention is shown which is particularly suited for low power and low cost implementation. Where the blocks of FIG. 8B have are the same as in FIG. 8A, the same reference designations have been used.

One of the more significant differences between the embodiment of FIG. 8A and that of FIG. 8B, is that the determination of the existence of an alarm condition is conducted in the unit 234 worn by the subject being monitored. Further, in order to keep the cost and power consumption of the system low, simpler diagnostic approaches are taken. As before, a set of sensors 236 sense physiological conditions of the subject. It is to be understood that these conditions can also include a caregiver call button (not shown) which can be activated by the subject being monitored in case of an emergency.

The sensors 236 provide signals representative of the physiological parameters being monitored, which signals are provided to diagnostics alarm block 238. Circuitry within this block determines whether an alarm condition exists in the parameters being monitored. When an alarm condition is detected, a signal is sent to the transmitter 240 which then sends an alarm condition signal to the base station 200. As shown in FIG. 8B, the telemetry path between the unit 234, worn by the subject being monitored, and the base station 200, can include a repeater 242 to extend the permissable separation between the base station and the subject being monitored.

In the embodiment of FIG. 8B, one of the techniques for reducing power consumption is to cause the transmitter 240 to be operational only when necessary: i.e., when an alarm condition exists. In such a mode, the transmitter 240 will preferably use the maximum amount of power available to it to provide as strong a signal level as possible to the base station. Under all other conditions, transmitter 240 is maintained in a quiescent state so that it consumes very little power. In this manner, the power source for unit 234 is used heavily only when an alarm condition exists.

In the preferred embodiment of the present invention the transmitter 240 provides a telemetry signal to the base station 200 which includes the identity of the patient from which the signal originates. It is to be understood that such identity can be provided by an appropriately coded digital word which is uniquely assigned to the patient wearing the unit 234. As such, the base station 200 need only detect the fact that an alarm condition exists, and then relay the identifying digital word to the caregiver 220.

In FIG. 8B, base station 200 includes a digital coincidence detector/encoder 255 which examines the signals from receiver 204 for the presence of various alarm digital words. These include a physiological alarm condition, a patient initiated alarm, and an out- o of-range alarm. Upon detection of one of the various alarm digital words, digital coincidence detector/encoder 255 will provide to the transmission paths an appropriate digital word. Such digital words can be provided by an appropriately programmed device such as part no. DC-7A, manufactured by Supertex of Sunnyvale, Calif.

In the embodiments.of FIG. 8B the link between the base station 200 and the caregiver unit 220 is the same as that embodiment in FIG. 8B.

Figure 9:
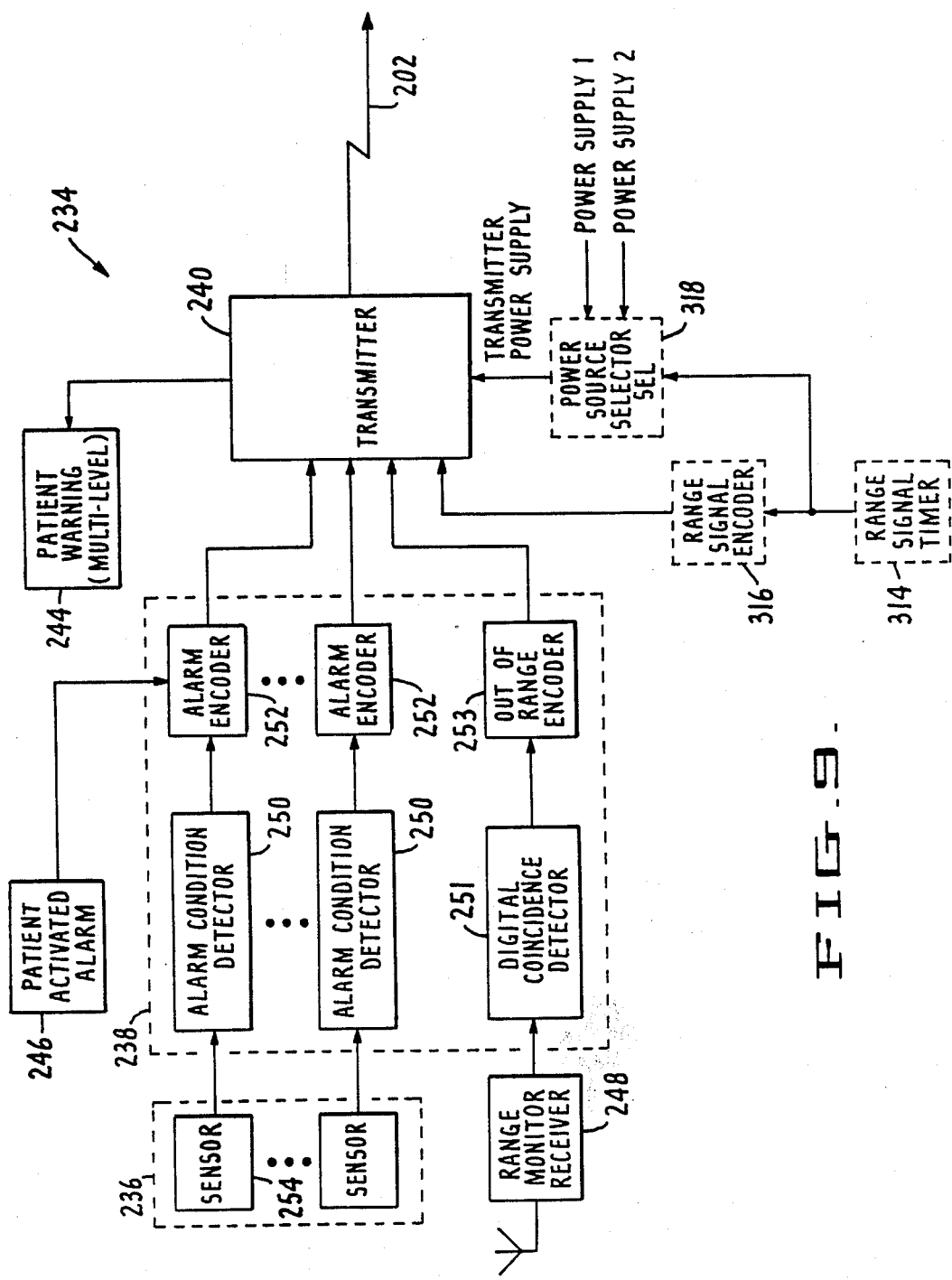
FIG. 9 is a more detailed block diagram of the sensor and diagnostics portion of the system worn on the patient.

Referring now to FIG. 9, a more detailed description of the sensor unit worn by the subject being monitored, will now be provided. Transmitter 240 can be similar to the transmitter 40 described in connection with FIG. 1 herein. As discussed above, transmitter 240 provides a telemetry signal 202 to base station 200. Also transmitter 240 activates a patient warning device 244 which can be a horn or other audio alarm to signal the patient that a condition which requires attention exists. The data transmitted by transmitter 240 is received from the diagnosticsalarm block 238. As shown in FIG. 9, these signals to be transmitted can come from a number of sources, including: sensors 236 worn on the subject to be monitored, a patient activated alarm 246, and a range monitor receiver 248. The sensors can include those described in connection with the sensor unit 10 of FIG. 1 herein.

Figure 10:
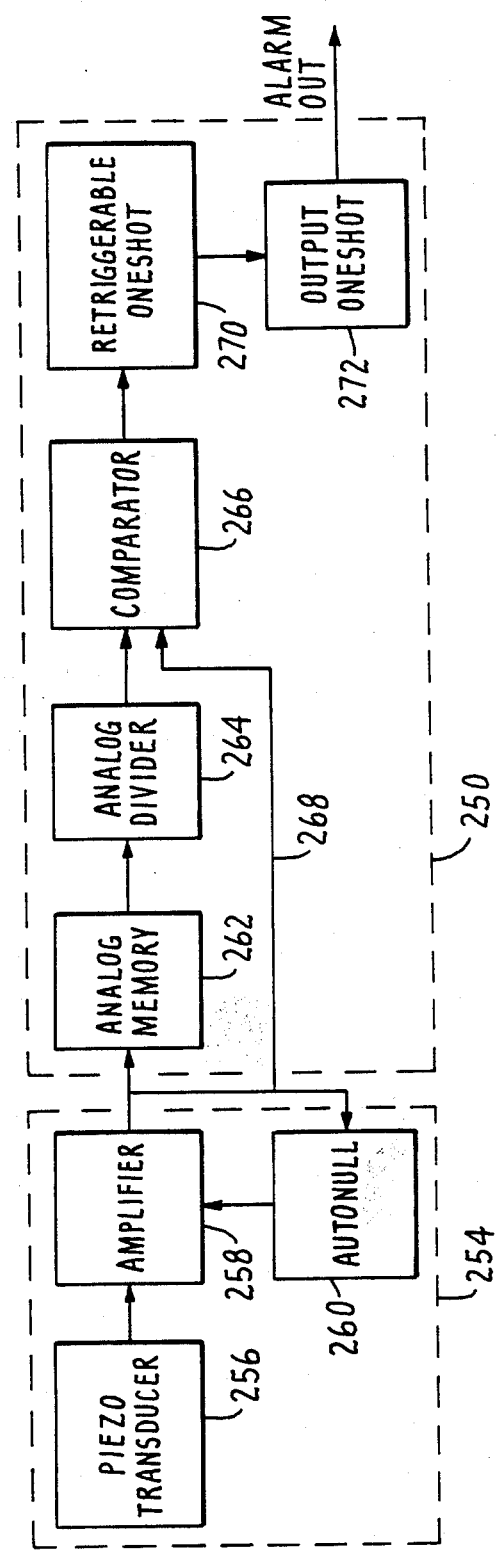
FIG. 10 is a more detailed simplified block diagram of an alarm channel of FIG. 9.

Referring now to FIG. 10, a more detailed block diagram of the alarm condition detector circuitry 250 is provided. Also shown in FIG. 10 is a more detailed block diagram of the sensor circuitry 254. Typically, the sensor circuitry includes a piezo electric transducer 256 providing a signal that is amplified by amplifier 258. The amplifier 258 has associated with it an autonull circuit 260 which provides offset correction for amplifier 258. Further details of the circuits were provided hereinabove, for example in connection with FIG. 3B.

Turning now to the alarm condition detector block 250, in the preferred embodiment of the present invention the functions of such block are provided by an analog adaptive threshold circuit. This circuit employs an analog memory 262 which receives a signal from sensor 254. This signal is then provided to analog divider 264 which applies a portion of the signal from analog memory 262 to comparator 266. Also shown provided as an input to comparator 266 is a signal directly from the sensor 254, via line 268. The analog memory operates much like a delay line so that the effect of the configuration is that comparator 266 compares a signal currently being received from sensor 254 with a signal stored in analog memory 262 that was received from the previous output of the sensor. The signal from analog divider 264 is used as a minimum level, above which comparator 266 provides a signal indicating that no alarm condition exists, and below which comparator 266 provides a signal indicating that an alarm condition exists.

Retriggerable oneshot 270 is coupled to the output of comparator 266 and is continually being reset by comparator 266 as long as a "no alarm" condition exists. Once comparator 266 detects an alarm condition retriggerable oneshot 270 will be permitted to change state, thereby activating output oneshot 272. The signal from output oneshot 272 activates alarm encoder 252, FIG. 9, which is configured to output a digital word descriptive of the alarm condition of the patient experiencing the alarm condition. Alarm encoder 252 can be provided by an appropriately connect integrated circuit such as part no. DC-7A, manufactured by Supertex of Sunnyvale, Calif.

It should be appreciated that the alarm condition detector 252 described in connection with FIG. 10 can be used to evaluate signals from a number of sources. Included are signals from range monitor receiver 248, FIGS. 8B and 9. The operation of the range monitoring circuitry will be described herein below.

Referring now to FIG. 11, a detailed schematic diagram of a preferred embodiment of the alarm condition detector 250 is provided. Also shown is a detailed schematic of the amplifier 258 and autonull 260 circuits.

Analog memory 262 can be implemented using amplifier device number ICL7641, manufactured by Maxim Integrated Products, Inc. of Sunnyvale, Calif. The circuit in the embodiment shown is configured so that a 10 microfarad capacitor is utilized as the primary storage elements and is coupled between ground and the inverting input to the amplifier device 273. The inverting input of the amplifier device 273 is connected to the device output by way of a diode 276. The cathode of diode 276 is connected to the inverting input of the device and to one end of the resistive divider which forms the analog divider circuit 264. The anode of diode 276 is connected to the output of amplifier 273. The noninverting input of amplifier 273 is connected to the cathode of diode 278 and to the intermediate point of a resistive divider formed by resistors 280 and 282. This resistive divider provides a threshold point which determines when diode 278 will conduct. The anode of diode 278 is connected to the output of the amplifier 258.

With the above configuration, capacitor 274 will be charged in a positive direction by positive going inputs to amplifier 273 which are sufficiently greater than the voltage then existing on capacitor 274. It is to be noted that because the potential at the inverting input is substantially equal to that at the noninverting input of amplifier 273, the voltage on capacitor 274 will "track" the voltage at the cathode of diode 278 when the voltage is moving in a positive direction.

Because of the presence of diode 276 in the circuit, movement of the cathode of diode 278 in the negative direction will cause diode 276 to be reverse biased and the voltage across capacitor 274 to be determined by the RC time constant of the discharge path through the analog divider 264. The RC time constant of interest is determined by the value of capacitor 274 times the sum of the resistors in the analog divider 264. It is to be understood that the typical physiological parameter being evaluated is periodic in nature and has a repetition rate on the order of a fraction of a period per second. The RC time constant is preferably set so that the discharging of capacitor 274 is slow enough to maintain the peak level of the signal period which just occurred, yet rapid enough to "track" any decreasing peak signals from the amplifier 258.

For example, where breath rates of 4 or 5 breaths per minute are being monitored, a time constant of 200 seconds can be used.

As discussed above, the analog divider 264 can be a resistive divider having resistors proportioned to one another to provide a desired fractional voltage of that stored in capacitor 274. In the embodiment shown in FIG. 11, this fraction is one half. It is to be understood that other fractions can be chosen depending upon the nature of the evaluation being conducted, the sensitivity desired, and the level of false alarms that can be tolerated.

The output of analog divider 264 is shown in FIG. 11 as being located at the junction of two ten megohm resistors. This output is coupled to the inverting input of amplifier 284. In the preferred embodiment of the present invention amplifier 284 can be device no. ICL7641. The noninverting input of amplifier 284 receives its input from the cathode of diode 278. The output of amplifier 284 is connected to its noninverting input so in such configuration a comparator circuit is provided. From the above it can be appreciated that this circuit compares the current voltage at the cathode of diode 278 with the divided peak voltage of the previous period of the signal being monitored. In this manner an adaptive threshold detector is provided which compares a current condition of the signal being monitored to a percentage of the previous peak condition of the signal being monitored. The output of amplifier 284 is coupled through a diode 286 to the trigger input of a retriggerable oneshot 270. This oneshot can be device no. 74HC123A, manufactured by Signetics Corporation of Santa Clara, Calif. The output of retriggerable oneshot 270 is coupled to an inverted trigger input of retriggerable oneshot 274. The width of the output pulses from oneshots 270 and 272 are determined by resistor 288/capacitor 290, and resistor 292/capacitor 294, respectively.

In the embodiment shown, an output from oneshot 270, which remains high, will not trigger oneshot 272. This occurs upon periodic retriggering of one shot 270. The RC time constant of resistor 288 and capacitor 290 is selected to be long enough so that oneshot can be retriggered by comparator 266 before its output pulse is completed.

Once the output of oneshot 270 goes low, oneshot 272 will be triggered to provide its output. This occurs when an alarm condition is detected; i.e. the current level of the signal is less than the fractional portion of the period of the signal preceding it. As long as the peak of the current period of the signal being monitored exceeds the fractional part of the previous period peak, comparator 266 will provide a positive going output at the frequency of the signal being monitored. When the signal does not exceed the threshold level, no positive going output is provided by comparator 266, and oneshot 270 "times out" to provide a negative going signal to oneshot 272.

In the above manner, any number of different kinds of periodic signals can be monitored using simple, low power circuitry.

Referring now to FIG. 12, the device worn by the caregiver will now be described in greater detail. As discussed earlier herein, the caregiver unit 222 has at least two distinct transmission paths from the base station. These paths carry the same information which include alarm signals indicating problems with the subject being monitored such as physiological problem or subject out of range problem as well as caregiver out of range signals.

In FIG. 12, one possible embodiment of the caregiver unit 220 is shown. For the carrier current transmission path, a carrier current antenna 294 receives the signal being radiated from the alternating current power lines 216 found throughout the building within which the system is located. The received signal is applied to regenerative amplifier 296. Regenerative amplifier 296 is of conventional design and has been chosen because of its low power requirements.

Regenerative amplifier 296 includes demodulator circuitry for extracting the transmitted information from the transmission signal. The transmitted data is supplied to a comparator 298 which squares up the signal and then supplies the squared up signal to decoder 228. A similar receiver scheme is found in the pager channel including pager antenna 300, receiver 302, and comparator 304. For the pager channel of the caregiver unit 220, a conventional pager receiver can be used.

Decoder 228 receives the signals from each of the carrier current and the pager channels, and compares these signals against selected codes which can include a patient code from patient code input circuit 306, and a range code from range code input 308. Each of these input circuits can take a number of forms including dip switches, magnetically encoded cards, read only memory and the like.

In operation, the user will select the patient code and the range code which corresponds to the patient sought to be monitored by the caregiver, and the base station from which the caregiver will be receiving information about the patient to be monitored. These codes are then placed into the code input circuits 306 and 308 for use by decoder 228.

Decoder 228 can be a parallel set of logic gates which compares the patient input codes against each of the series of signals being received on the carrier current path and the pager path. When a particular code is found in the signal stream, the appropriate alarm is sounded. As shown in FIG. 12, an out-of-range alarm 310 is provided and a patient alarm 312 is provided. Preferably, each of these alarms is distinct so that the caregiver can distinguish between the two without the need for additional information.

The out-of-range alarm circuit 310 includes a series of retriggerable one shots operating in a manner like one shots 270 and 272, previously described. The output one shot then activates the out-of-range alarm to alert the caregiver that the caregiver is out of range.

Returning to FIGS. 8A and 8B, the out-of-range detection circuitry will be described in further detail. In FIG. 8A, the base station 200 is shown including a range signal generator 232. This range signal generator provides a signal which is transmitted by the base station to the caregiver unit 222 over the pager path 218 and the carrier current path 220. This range signal is a range signal code which is received by the caregiver unit 222.

While the range signal code is shown in FIG. 8A as being transmitted only to the caregiver unit 222, it is within the scope of the present invention to also provide and transmit a range signal code to the sensor unit 10 worn by the subject being monitored. This is shown in FIG. 8B and FIG. 9.

In FIG. 8B, the range monitor receiver 248 in the subject unit 234 can be similar to that used in the carrier current receiver 226, FIG. 12. The output of the range monitor receiver 248 is applied to digital coincidence detector circuitry 251, which activates an out-of-range encoder 253 when an out-of-range condition is detected. An out-of-range condition exists when the digital word received from range monitor receiver 248 does not match a predetermined range code that is resident in digital coincidence detector 251. Out-of-range encoder 253, when activated, provides a serial, digital word for transmission by transmitter 240. This word indicates an out-of-range condition for the particular patient, and includes the patient identity.

An alternate technique for range detection is shown in FIG. 9. The boxes shown in dashed format provide a range signal which is generated at the subject being monitored and detected at the base station. A range signal timer 314 provides a periodic, enabling signal which activates range signal encoder 316 to provide a serial digital word for transmission by transmitter 240. At the same time range signal encoder 316 is activated, power selector block 318 modifies the validity of power supplied to transmitter 240.

As shown in FIG. 9, power source selector block 318 receives a power supply 1 and power supply 2 voltage. Preferably, these voltages are selected so that, when the transmitter transmits using the power supply 1 voltage, it is transmitting with the highest power available. Conversely, when the transmitter 240 transmits with the power supply 2 voltage, a much lower power level is transmitted by transmitter 240. The power source selector circuit 318 selects the power supply 2 voltage to be applied to transmitter 240 when the range signal encoder 316 supplies the serial digital word to transmitter 244 transmission. This conserves power for longer battery life.

With the alternative embodiment shown in FIG. 9 for the range detection scheme, it is to be understood that the base station 200 will include an alarm condition detector 250 type circuit for evaluating the validity of the range signal being received at the base station 200 from the subject unit 234. Preferably, range signal timer 314 enables range signal encoder 316 every 30 seconds.

In operation, the system of the present invention provides a link between the caregiver and the subject being monitored which utilizes an intermediate base station and redundant signal paths between the base station and the caregiver. The caregiver wears a unit which receives signals from the base station. Signals from the base station provide information about the subject being monitored and provide signals for use in determining whether the caregiver remains within the range of the base station. The unit worn by the subject being monitored can include diagnostic circuitry for evaluating signals received from sensors to transmit an alarm signal to the base station when the subject being monitored is in need of assistance. A range monitoring system is provided which will alert the subject being monitored as well as the caregiver whenever the subject being monitored moves outside the range of the base station.

The carrier current transmitter can utilize device number LM1893, manufactured by National Semiconductor Corporation of Santa Clara, Calif., and more specifically the transmitter scheme shown in FIG. 3 of the data sheet for the device published in the National Semiconductor Corporation 1984 Linear Supplement Databook, page S12-67, et seq. However, the carrier current receiver, as shown in FIG. 3 of the data sheet will not be utilized, since the power line itself will be used as a localized transmitting antenna. The signal radiated from the AC power line 216 will be received by the carrier current receiver antenna, as if the signal were a radio signal.

It should be understood that various alternatives to the embodiment shown herein may be employed in practicing the present invention. It is intended that the following claims define the invention, and that the structure within the scope of these claims and their equivalents be covered thereby.

What is claimed is:

1. An apparatus for notifying an ambulatory caregiver of the physical condition of a patient, comprising monitoring means positionable on the patient and responsive to the physical condition of the patient for determining whether the ambulatory caregiver should be notified and for transmitting a caregiver notification signal when it is determined that the ambulatory caregiver should be notified;

base station means positionable apart from the patient and responsive to the transmitted caregiver notification signal for relaying the transmitted caregiver notification signal over a plurality of redundant but independent transmission paths; and receiver means positioned apart from the base station means and positionable on the ambulatory caregiver and responsive to the transmitted caregiver notification signal as relayed by the base station means over each of the plurality of redundant but independent transmission paths for providing a predetermined indication to the ambulatory caregiver that a Caregiver notification signal has been received.

2. The apparatus of claim 1, wherein the redundant but independent transmission paths include a carrier current path and a pager path.

3. The apparatus of claim I, further including means for determining whether the patient is within a predetermined proximity of the base station means.

4. The apparatus of claim 3, wherein the proximity determining means comprises means located in the monitoring means for periodically providing a predetermined code which is transmitted by the monitoring means to the base station means; and means located in the base station means and responsive to the predetermined code for determining when the predetermined code has not been received from the monitoring means within a predetermined time period.

5. The apparatus of claim 1, wherein the monitoring means includes sensor means positionable on the patient for sensing a physiological parameter of the patient;

analysis means responsive to the sensor means for providing an alert indication when the sensed physiological parameter of the patient fails to meet predetermined criteria; and means coupled to the analysis means for transmitting the caregiver notification signal to the base station when the alert indication is received from the analysis means.

6. The apparatus of claim 5, wherein the physiological parameter being monitored is periodic and the sensor means provide an electrical sensor signal of varying amplitude which is indicative of the monitored physiological parameter, and further wherein the analysis means is an analog adaptive threshold circuit including means responsive to electrical signals from a reference period of the electrical sensor signal for capturing a peak of the electrical signals from the reference period;

means responsive to electrical signals from a comparison period of the electrical sensor signal, wherein the comparison period immediately follows the reference period, for capturing a peak of the electrical signals from the comparison period; and means for providing the alert indication when the peak of the electrical signals from the comparison period is less than a predetermined fraction of the peak of the electrical signals from the reference period, and wherein the comparison period is used as the reference period for a subsequent comparison when the peak of the electrical signals of the subsequent period is not less than the predetermined fraction of the peak of the electrical signals of the reference period.

7. An apparatus for notifying an ambulatory caregiver of the physical condition of a patient, comprising monitoring means positionable on the patient for obtaining and transmitting physiological data from the patient;

base station means positioned apart from the patient and responsive to the physiological data transmitted by the monitoring means, including means for determining whether the ambulatory caregiver should be notified and for transmitting a caregiver notification signal over a plurality of redundant but independent transmission paths when it is determined that the caregiver notification signal should be given; and receiver means positioned apart from the base station means and positionable on the ambulatory caregiver and responsive to the caregiver notification signal as transmitted by the base station means over each of the independent transmission paths for providing a predetermined indication to the ambulatory caregiver that a caregiver notification has been received.

* * * * *

UNITED STATES PATENT AND TRADEMARK OFFICE
CERTIFICATE OF CORRECTION

PATENT NO. : 4,827,943

DATED : May 9, 1989

INVENTOR(S) : Robert Bornn, Robert D. Ricks

It is certified that error appears in the above - identified patent and that said Letters Patent is hereby corrected as shown below:

On the title page:

Page 1, line 6, delete "abandoned" and substitute --U.S. Patent No. 4,784,162--.

Signed and Sealed this

Twenty-third Day of October, 1990

Attest:

HARRY F. MANBECK, JR.

*Attesting Officer*    *Commissioner of Patents and Trademarks*